(12) United States Patent
Kleckner et al.

(10) Patent No.: US 6,889,083 B2
(45) Date of Patent: May 3, 2005

(54) ATRIAL TRACKING RECOVERY TO RESTORE CARDIAC RESYNCHRONIZATION THERAPY IN DUAL CHAMBER TRACKING MODES

(75) Inventors: Karen J. Kleckner, New Brighton, MN (US); Robert A. Betzold, Fridley, MN (US); Thomas G. Lynn, Jr., West Chester, PA (US)

(73) Assignee: Medtronic, Inc., Minneapolis, MN (US)

( * ) Notice: Subject to any disclaimer, the term of this patent is extended or adjusted under 35 U.S.C. 154(b) by 57 days.

(21) Appl. No.: 10/419,593

(22) Filed: Apr. 21, 2003

(65) Prior Publication Data

US 2004/0210264 A1 Oct. 21, 2004

(51) Int. Cl.[7] .............................................. A61N 1/365
(52) U.S. Cl. ...................................................... 607/25
(58) Field of Search ........................... 607/4, 9, 14, 17, 607/25

(56) References Cited

U.S. PATENT DOCUMENTS

| 3,937,226 | A |   | 2/1976  | Funke .......................... 607/14 |
| 5,174,289 | A |   | 12/1992 | Cohen ........................... 607/9  |
| 5,247,929 | A | * | 9/1993  | Stoop et al. .................. 607/14 |
| 5,267,560 | A |   | 12/1993 | Cohen .......................... 607/25 |
| 5,269,299 | A | * | 12/1993 | Duncan ......................... 607/9  |
| 5,403,356 | A |   | 4/1995  | Hill et al. ................... 607/14 |
| 5,514,161 | A |   | 5/1996  | Limousin ....................... 607/9  |
| 5,514,163 | A |   | 5/1996  | Markowitz et al. ............ 607/9  |
| 5,584,867 | A |   | 12/1996 | Limousin et al. ............. 607/9  |
| 5,609,610 | A |   | 3/1997  | Nappholz ....................... 607/9  |
| 5,626,623 | A |   | 5/1997  | Kieval et al. ................. 607/23 |
| 5,653,738 | A |   | 8/1997  | Sholder ........................ 607/14 |
| 5,674,259 | A |   | 10/1997 | Gray ............................ 607/20 |
| 5,720,768 | A |   | 2/1998  | Verboven-Nelissen ......... 607/9  |
| 5,741,309 | A |   | 4/1998  | Maarse ......................... 607/9  |
| 5,792,203 | A |   | 8/1998  | Schroeppel .................. 607/30 |
| 5,797,970 | A |   | 8/1998  | Pouvreau ...................... 607/9  |
| 5,814,083 | A | * | 9/1998  | Hess et al. .................... 607/14 |
| 5,902,324 | A |   | 5/1999  | Thompson et al. ............ 607/9  |
| 6,070,100 | A |   | 5/2000  | Bakels et al. ................. 607/9  |
| 6,128,533 | A | * | 10/2000 | Florio et al. .................. 607/9  |
| 6,129,744 | A |   | 10/2000 | Boute .......................... 607/25 |
| 6,167,307 | A |   | 12/2000 | Hess ............................ 607/9  |
| 6,256,536 | B1|   | 7/2001  | Kramer ......................... 607/9  |
| 6,311,088 | B1| * | 10/2001 | Betzold et al. ............... 607/14 |

* cited by examiner

*Primary Examiner*—Carl Layno
(74) *Attorney, Agent, or Firm*—Paul H. McDowall; Girma Wolde-Michael

(57) ABSTRACT

A feature named "atrial tracking recovery" (ATR) provides for restoring delivery of cardiac pacing therapy upon identification of an atrial refractory sense-ventricular sense (AR-VS) pattern of cardiac activity. In one embodiment, such patterns are monitored to determine if they are terminable. Once the AR-VS pattern is identified, the then operative post-ventricular atrial refractory period (PVARP) is shortened to allow sensing of the atrial event, which previously was unable to initiate a sensed atrioventricular (SAV) interval. Subsequent SAV intervals are shortened until an atrial event is sensed so that a ventricular pacing stimulus is delivered after the SAV interval expires. Since the SAV interval is normally programmed to an interval that is shorter than the intrinsic conduction time, ventricular pacing stimulus is provided after the SAV ends, thereby effectively restoring delivery of a ventricular pacing modality such as cardiac resynchronization therapy (CTR).

12 Claims, 5 Drawing Sheets

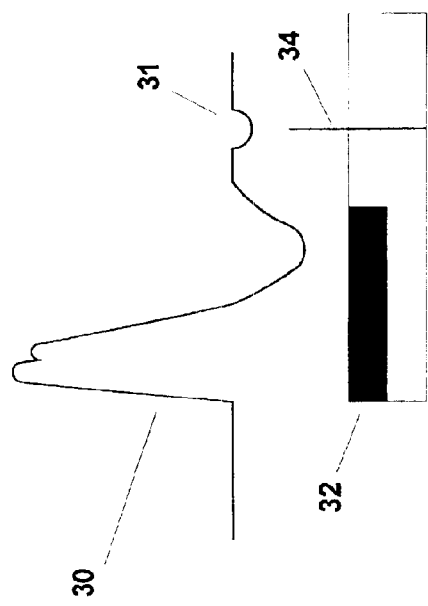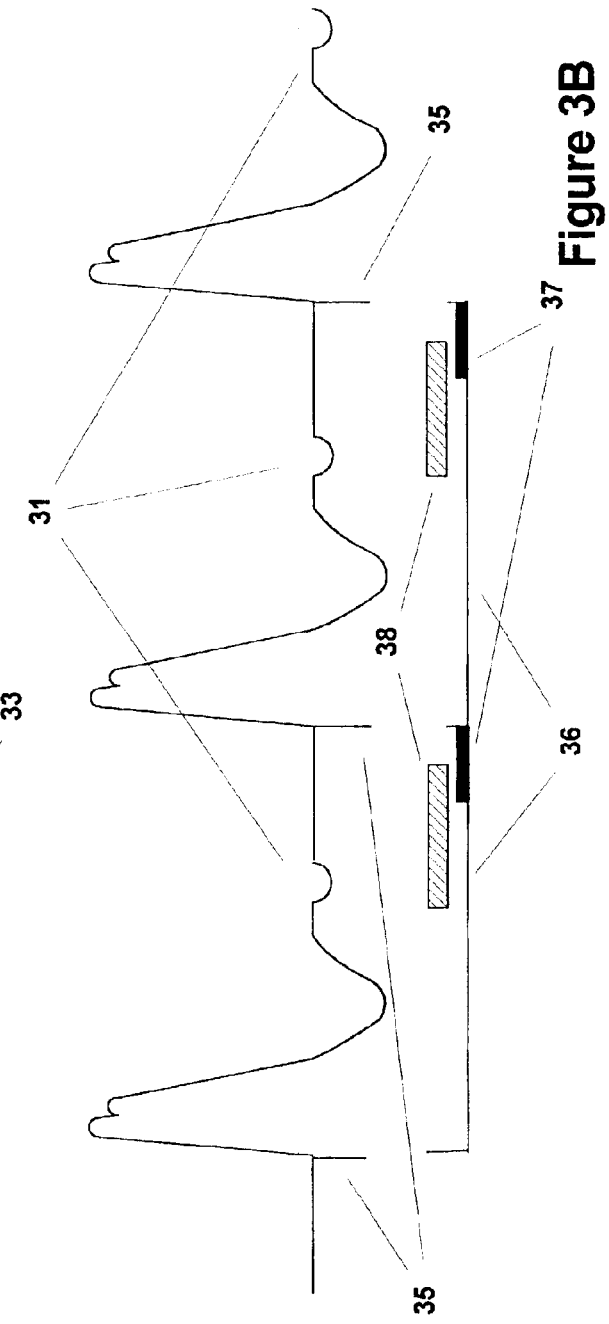

ATRIAL TRACKING RECOVERY TO RESTORE CARDIAC RESYNCHRONIZATION THERAPY IN DUAL CHAMBER TRACKING MODES

FIELD OF THE INVENTION

The present invention pertains to multi-site ventricular pacing systems, and particularly to Bi-Ventricular cardiac pacing systems that pace and sense in at least one atrial heart chamber and deliver synchronized ventricular pacing pulses to right ventricular (RV) and left ventricular (LV) sites. More particularly, it pertains to tracking modes, that is, those that sense spontaneous atrial events that start a sensed AV interval and culminate in ventricular paced events or native ventricular depolarizations. Even more particularly, it pertains to the adjustment of the total atrial refractory period (TARP) to ensure the delivery of pacing to both the right and left ventricles following the sensing of native atrial events.

BACKGROUND OF THE INVENTION

When functioning property, the human heart maintains its own intrinsic rhythm and will pump an adequate supply of blood throughout the body's circulatory system. However, some individuals have cardiac arrhythmias and/or disease states that result in diminished blood circulation. One method of treating cardiac arrhythmias is the administration of drug therapy. Another method is the use of a cardiac rhythm management system. Such systems (pacemakers, cardioverters, among others) are usually implanted in the patient and deliver electrical stimulation therapy directly to the heart.

One type of cardiac disturbance faced by cardiac rhythm management systems is congestive heart failure (CHF). CHF is a condition in which the muscles in the walls of the right and/or left sides of the heart are stretched abnormally with each cardiac filling and contraction. As a result, the left atrium and left ventricle become enlarged, and the heart muscle possesses less contractility, a condition called left ventricular dysfunction (LVD). LVD decreases cardiac output, which, in turn, often results in an increased heart rate with less resting time between contractions. The heart consumes more oxygen, and its condition, along with the patient's, typically worsens over a period of time.

When the left side of the heart has become enlarged due to CHF, the ventricular depolarization signals may travel through and depolarize the left side of the heart more slowly than they do in the right ventricle. As a result, the left and right ventricles do not contract simultaneously. Rather, the left ventricle contracts somewhat later than the right ventricle. This further reduces the pumping efficiency of the heart.

As a result, there has been a need to provide CHF patients with a pacing therapy that coordinates ventricular contractions or otherwise increases the heart's pumping efficiency. Moist recently, atrial synchronous pacing that provides simultaneous pacing pulses to both right and left ventricles has met this need.

In general, LVD with conduction disturbances patients benefit from pacing pulses applied simultaneously in both right and left heart chambers. These ventricular pacing pulses must be delivered in synchrony with atrial paced or sensed depolarizations detected at the atrial electrode site(s). The programmed AV interval durations following atrial paced or sensed events must also be short enough to rule out spontaneous, conducted R-waves. Atrial and left ventricular cardiac output can be significantly improved when left and right chamber synchrony is restored, particularly in patients suffering from dilated cardiomyopathy, LVD, and CHF.

A number of proposals have been advanced for providing pacing therapies to alleviate heart failure conditions and restore synchronous depolarization and contraction of a single heart chamber, right and left, or upper and lower heart chambers as described in detail in the commonly assigned U.S. Pat. No. 6,129,744 and in commonly assigned U.S. Pat. Nos. 5,403,356, 5,797,970, 5,902,324, and 6,070,100 and U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867. Maintenance of AV mechanical synchrony is of great importance as set forth in greater detail in commonly assigned U.S. Pat. No. 5,626,623, incorporated herein by reference in its entirety.

Other intervals timed by the implantable pulse generator (IPG) include atrial and ventricular sense amplifier blanking periods following delivery of atrial and/or ventricular pacing pulses to disable atrial and ventricular sensing. In addition, sense amplifier refractory periods are timed out following atrial and ventricular paced and sensed event signals. Such "refractory" A-SENSE and V-SENSE signals are selectively ignored or employed in a variety of ways to reset or extend time periods. An atrial refractory period (ARP) extends for various time durations through the Sensed AV (SAV) delay or the Paced AV (PAV) delay.

In addition, a post-ventricular atrial refractory period (PVARP) begins at a V-PACE pulse or V-SENSE. A-SENSE signals sensed during the PVARP are noted but do not start an AV interval. The rationale for this operation is that such events may be a retrograde atrial sensed event or an event that is part of an atrial tachycardia episode. In either case, it is not desirable to synchronize ventricular pacing to such events. The duration of the PVARP may be fixed by programming, extended after a premature ventricular contraction (PVC), or vary as a function of the pacing or heart rate, with the result that in many cases relatively long PVARPs are in effect at lower rates.

The atrial tracking VDD/R and DDD/R pacing modes function in the above-described manner and additionally provide rate modulation of a ventricular pacing escape interval between a programmable lower rate and an upper rate limit (URL). The URL may either be the upper tracking rate (UTR) or upper sensor rate (USR). At times when the intrinsic atrial rate is increasing due to exertion, the SAV is extended to prevent the ventricular pacing rate from exceeding the UTR through an operation commonly termed "Pacemaker Wenckebach." The atrial rate, however, may continue to rise until native atrial events fall into the PVARP. At such times, if the patient has a conduction block, the ventricular paced beat is "blocked" since the refractory sensed atrial event cannot start an SAV interval. If, however, the patient has an intact AV conduction system, a native ventricular depolarization may occur. This operation is described in U.S. Pat. No. 6,256,536 which is incorporated herein by reference in its totality.

The disruption of AV electrical and mechanical synchrony frequently arises due to the spontaneous depolarization of the ventricles triggered at an ectopic site in one of the ventricles. Such a spontaneous depolarization that is not associated with a prior atrial depolarization is characterized as a PVC. Many of the problems resulting from the occurrence of a PVC in a patient with a dual chamber pacemaker are described more fully in U.S. Pat. Nos. 4,788,980 and 5,097,832, both of which are incorporated herein by reference. One such problem is the initiation of a pacemaker mediated tachycardia or PMT. The most commonly employed PVC response to prevent initiation of PMT is to extend the PVARP to a programmed duration, such as 400–500 ms, in response to the PVC. Moreover, a "pacemaker-defined" PVC is defined as the second of two ventricular events without an intervening atrial event. Such a pacemaker-defined PVC also extends an associated PVARP to 400, 500, or more milliseconds (ms). The PVARP extension masks atrial sensed signals that are presumed to result from retrograde conduction during this period of time as disclosed in the above-incorporated '980 patent. Numerous other patents have dealt with varying the PVARP in an attempt to prevent instigating a PMT, including U.S. Pat. Nos. 6,167,307, 5,653,738, 4,920,965, 4,554,921, 5,123,412, and 4,503,857, all incorporated herein by reference in their entireties.

Unfortunately, in some circumstances prolongation of the PVARP in response to a PVC or prolongation of the SAV interval (Wenckebach operation) has unfortunate consequences. Even though a possible PMT is prevented, loss of normal P-wave tracking [atrial sense-ventricular pace (AS-VP)] may occur because the P-wave occurs during the PVARP.

If the subsequent PVARP is long enough, a P-wave may fail to initiate an SAV delay. If, however, normal AV conduction is present, a native ventricular depolarization will occur [atrial refractory (AR-VS)]. Such native ventricular depolarization, however, interrupts CHF therapy that requires ventricular pacing. Loss of this type of atrial synchrony may extend over a period of time (e.g., seconds to hours) depending on the pacemaker's programmed rate settings and the patient's sinus rate (i.e., the P-wave rate set by the SA node). Ventricular pacing remains inhibited until either the occurrence of an non-refractory sensed atrial depolarization or delivery of an atrial pacing pulse outside the total atrial refractory period (TARP).

A similar problem may arise in response to other events that disrupt AV synchrony. Additional events which disrupt AV synchrony include, among others, premature atrial contractions, noise sensing and associated asynchronous pacing, also known as "noise reversion" and other pacing mode or operation changes, including those arising from mode switching, telemetric programming (e.g., placing a magnetic field proximate a pacemaker), removal of a magnetic field, "cancel magnet" commands, device programming and downlink telemetry functions. In particular, changes from non-atrial synchronized pacing modes to atrial synchronized pacing modes or from non-atrial synchronized operation to atrial synchronized operation within an atrial synchronized pacing mode have the potential to disrupt AV synchrony. Prolongation of PVARP in response to such disrupting events is disclosed in U.S. Pat. No. 4,554,920, also incorporated herein by reference in its entirety.

In modern dual chamber pacemakers, the programmed initial PVARP may vary as a function of the heart rate or sensor rate. In the context of these types of pacemakers, the relatively long PVARPs that may be in effect at lower rates can, in the same fashion, result in persistent loss of AV synchrony as described above. A method, that resolves these issues for most implantable medical devices (IMDs), but not CHF devices, has been disclosed in U.S. Pat. No. 6,311,088, incorporated herein by reference in its entirety.

U.S. Pat. No. 5,741,309 provides one solution to correcting this problem in CHF IMDs. This patent employs the term PR+PVARP block to define the conduction of an AR event to the ventricles resulting in a ventricular sense. The solution is stated as follows: "After a predetermined number of cycles where an atrial event is sensed during a PVARP, the pacemaker is programmed to ignore or shorten the PVARP and/or URI, pacing the ventricles after the next sensed AV event thereby breaking the PR+PVARP block." While shortening the PVARP or upper rate interval may be applicable, the inventors of the present invention believe that ignoring or shortening either or both may lead to other pacing problems during the time that either or both are ignored or shortened. Otherwise, this patent disclosure offers little detail on how or when the programmed PVARP or URI is restored.

Holter recordings have revealed extended periods of time during which cardiac resynchronization therapy (CRT) is not continuously delivered. For the purposes of the present disclosure CRT can be considered a form of triple chamber, synchronized bi-ventricular pacing. The cardiac rhythm that was observed to cause this lack of continuous CRT delivery was atrial refractory sense to ventricular sense (AR-VS). That is, whenever an atrial event falls within the refractory portion of the PVARP it cannot start an AV interval and, thus, cannot be tracked. There are several causes that may start such a rhythm and may be listed, among others, as follows.

The patient's atrial rate exceeds the programmed upper tracking rate (UTR). As a result, atrial events fall within the PVARP. As a result and assuming the presence of intrinsic AV conduction, the atrial depolarization is conducted to the ventricle(s), resulting in an intrinsic ventricular depolarization. Since the intrinsic AV conduction is longer than the programmed SAV, the overall TARP (AV conduction and PVARP) causes the next atrial event to occur during the PVARP, and, though sensed during the PVARP, no SAV interval is initiated. Once this cardiac rhythm pattern (AR-VS) is established, the atrial rate must decrease to the point that the atrial event no longer falls into the PVARP in order for the AR-VS pattern to terminate. That is, as soon as an atrial event is sensed outside of refractory, a SAV is initiated and tracking restored. For example, with intrinsic AV conduction of 300 ms and a PVARP programmed to 310 ms, the atrial rate must fall below 100 bpm before atrial tracking is restored, thereby resuming CRT delivery.

Multiple PVCs or PVC couplets may also cause an AR-VS pattern. Although the first PVC may trigger a long PVARP, e.g., 400 to 500 ms, the P-wave that falls into the refractory period may be conduced to the ventricles, leading to an AR-VS pattern.

Similarly, an undersensed atrial event that conducts, resulting in an R-wave that is a "pacemaker-defined" PVC, may cause the next atrial event to occur during a PVARP and bring about a second conducted R-wave. The AR-VS pattern may continue if the patient's atrial rate is fast enough.

An atrial tachyarrhythmia may often result in an AR-VS pattern with a rate faster than the UTR. If the tachyarrhythmia breaks with the atrial rate slowing below the UTR, the first atrial depolarization may occur during a refractory period and start the AR-VS pattern.

What is needed, then, is a method for identifying the AR-VS pattern and restoring atrial tracking as quickly as possible. Thus, the basis for the loss of cardiac resynchronization therapy is resolved.

SUMMARY OF THE INVENTION

A feature named "atrial tracking recovery" (ATR) provides a means of restoring cardiac resynchronization therapy (CRT) delivery upon identification of an AR-VS pattern of cardiac activity. The present invention incorporates a method and technique to monitor for the presence of such sequences to determine if they are terminable. Once the AR-VS pattern is identified, according to the present invention the PVARP is shortened to allow sensing of the atrial event, which previously was unable to initial an SAV interval. Subsequent SAV intervals are shortened even more as the intervention proceeds in an attempt to terminate the AR-VS pattern. The shortening of the SAV interval, however, is a function of the UTR behaviour. Since the SAV interval is normally programmed to an interval that is shorter than the intrinsic conduction time, ventricular pacing stimulus is provided at the end of the SAV, thereby effectively restoring CRT.

ATR functions only in atrial tracking modes (e.g., DDD/R and DDI/R) and may be in one of three states: (i) monitor only, (ii) intervention, and (iii) suspended. ATR is automatically suspended during temporary operations and during a mode switch operation, during which the IMD switches to a non-tracking mode, such as DDI, VVI, among others, in the presence of an atrial tachycardia. Otherwise, when programmed "on," ATR is in its monitor-only state, and is not intervening.

A transition from monitor to intervention occurs when all of the following are true for eight consecutive pacing cycles: 1) The operational pacing mode is able to track atrial depolarizations, that is, not in mode switch; 2) The ventricular event is sensed (VS); 3) The most recent V-V interval contained only one atrial event, an atrial refractory sense (AR); 4) The most recent AR-AR interval has no more than a predetermined difference (in ms) of duration from the preceding AR-AR interval; 5) The most recent AR-AR interval is a predetermined interval less than the UTR interval; 6) The most recent AR-AR interval is greater than the sum of the operating SAV interval and the operating PVARP; and 7) The most recent VS-AR interval is greater than post-ventricular atrial blanking (PVAB) interval.

Typically and as employed elsewhere in this patent disclosure, an atrial sensed event that occurs during a PVARP is represented by the notation "AR." In patients having intact AV conduction, such an atrial event may conduct through the AV node and HIS-Purkinje conduction system resulting in a sensed intrinsic ventricular depolarization (VS). When these two events occur (AR-VS), ATR is invoked and begins monitoring for the presence of the seven criteria listed in the previous paragraph. If the above-noted seven criteria and the AR-VS pattern are present for eight consecutive cardiac cycles, the ATR algorithm dictates instructions to shorten the TARP, that is, the sum of the PVARP and SAV. In general, the PVARP is shortened only as much as is necessary to allow tracking of the next P-wave, without violating the UTR. If one or more shortenings of these intervals result in a ventricular pace (VP), the AR-VS pattern is terminated and the ATR intervention is halted and the cardiac pacing engine returns to its monitor state. On the other hand, if successive shortening of the PVARP fails to result in a VP, ATR intervention is aborted. In such cases, a flag is set in the device's memory to trigger a report to upon next interrogation of the pacing engine and certain data related to the attempted ATR intervention may be stored for later retrieval. Or, if the device is equipped with a patient alert system, when the ATR is halted an audible, tactile and/or visible cue is triggered signaling the patient to take action, such as calling an attending physician for an appointment, or going to the hospital, among others.

BRIEF DESCRIPTION OF THE DRAWINGS

These and other advantages and features of the present invention will be more readily understood from the following detailed description thereof, when considered in conjunction with the drawings, in which like reference numerals indicate identical structures throughout the several views, and wherein:

FIG. 3A is a representational drawing of ECG/EGM traces of cardiac activity showing a post-ventricular contraction (PVC) followed by a retrograde atrial event and a PVARP (box) and illustrating a retrograde atrial event occurring during a PVARP.

FIG. 3B is a representational drawing of ECG/EGM traces of cardiac activity showing a pacemaker-mediated tachycardia (PMT) that can result from a retrograde atrial event.

DETAILED DESCRIPTION OF THE DRAWINGS

It should be appreciated that the present invention may be utilized particularly to treat patients of suffering CHF and bradycardia. The pacing system of the present invention may also be incorporated into an anti-tachyarrhythmia system including specific high rate pacing and cardioversion shock therapies for providing staged therapies to treat a diagnosed arrhythmia.

Figure 1:
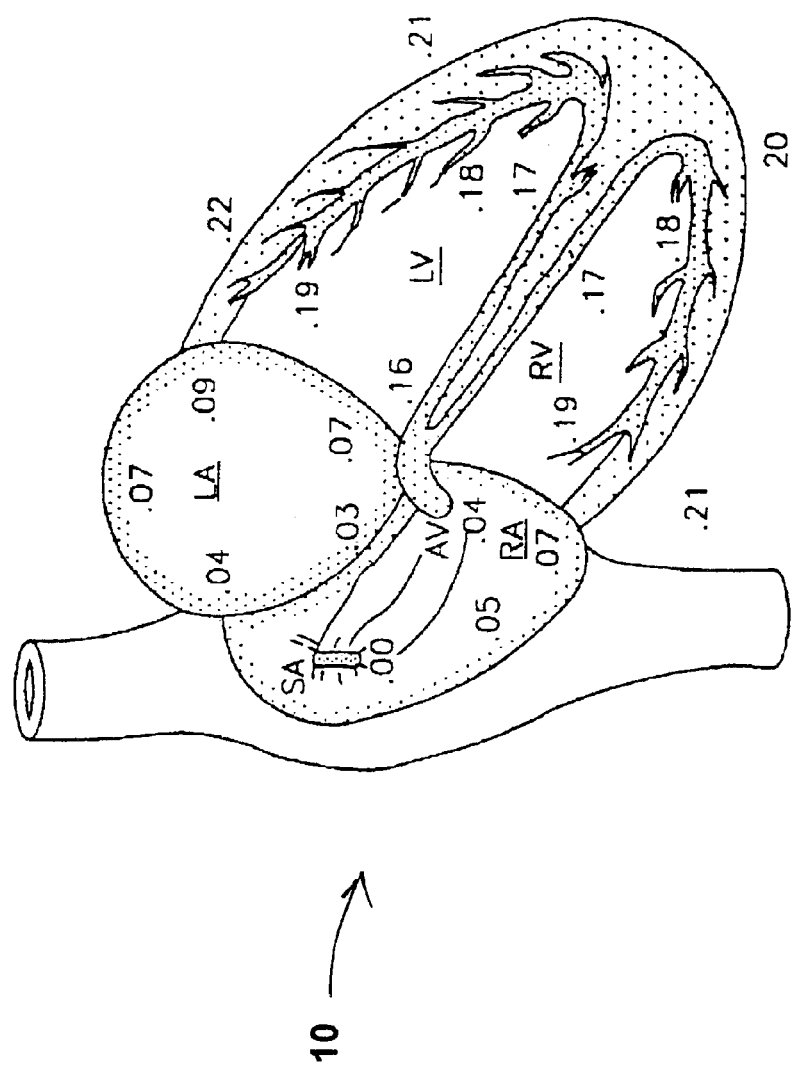
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV). These vessels provide for blood flow and pumping following depolarization. The sino-atrial node (SA) and atrio-ventricular node (AV), along with the His-Purkinje system comprise the heart's conduction system that transmits electrical signals to trigger the various chambers to contract in a sequential manner.

FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of an electrical impulse at the SA Node in the right atrial wall and its transmission through the atrial conduction pathways of Bachmann's Bundle and the Internodal Tracts from the right atrium into and through the atrial septum to the left atrium. The SA depolarization impulse reaches the Atrio-ventricular (AV) node and the atrial septum within about 40 msec and reaches the furthest walls of the RA and LA within about 70 msec, after which the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent to the RA or LA is also referred to as a sensed P-wave. Although the location and spacing of the external ECG electrodes or implanted unipolar atrial pace/sense electrodes has some influence, the normal P-wave width normally does not exceed 80 msec in width as measured by a high impedance sense amplifier coupled with such electrodes. A normal near field P-wave sensed between closely spaced bipolar pace/sense electrodes and located in or adjacent the RA or the LA usually has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje network over the remaining 40 msec. The aggregate RV and LV depolarization wave and the subsequent T-wave signaling repolarization of the depolarized myocardium are referred to as the QRST portion of the PQRST cardiac cycle complex when sensed across external ECG electrodes and displayed. When the amplitude of the QRS ventricular depolarization wave passing access a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence, the normal R-wave width is about 80 msec in width as measured by a high impedance sense amplifier. A normal near field R-wave sensed across closely spaced bipolar pace/sense electrodes and located in or adjacent the RV or the LV usually has a width of about 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak-to-peak asynchrony can range from 80 to 200 msec or longer. In RBBB and LBBB patients, the QRS complex is widened far beyond the normal range from >120 msec to 250 msec as measured on surface ECG. This increased width demonstrates the lack of synchrony of the right and left ventricular depolarizations and contractions.

In accordance with a preferred embodiment of the present invention, a method and apparatus is provided to restore the depolarization sequence of FIG. 1 and the synchrony between the right and left ventricular heart chambers that contributes to adequate cardiac output. This restoration is effected through providing optimally timed cardiac pacing pulses to the right and left ventricles simultaneously while maintaining AV synchrony. The present invention helps ensure the simultaneous presence of ventricular pacing pulses that must be present to provide CRT.

Figure 2:
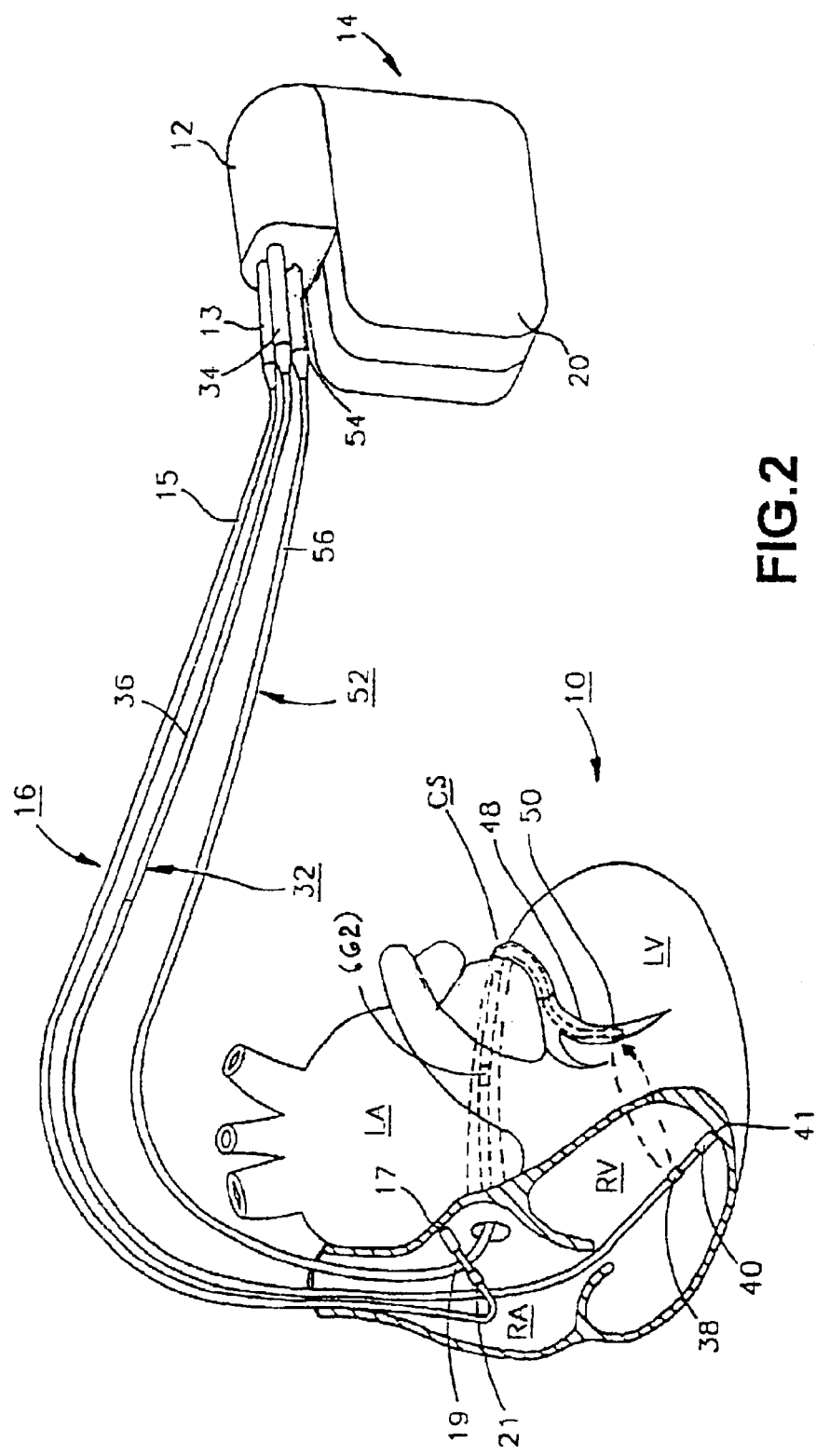
FIG. 2 is a perspective view in partial cross-section with parts removed depicting a three chamber (i.e., atrial and bi-ventricular chamber-based leads) pacing system operatively coupled to the right atrial chamber and both ventricular chambers of a graphically depicted heart.

FIG. 2 is a schematic representation of an implanted, three channel cardiac pacemaker of the above noted types for restoring AV synchronous contractions of the atrial and ventricular chambers with simultaneous biventricular pacing of the right and left ventricles. The Implantable Pulse Generator IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. For instance, any of the leads may be placed epicardially if desired, or there may be other arrangements made. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lad 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrodes (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV Coronary Sinus (CS) lead 52 is passed through a vein and the RA chamber of the heart 10, into the CS and then inferiorly in a branching vessel of the cardiac vein 48 to extend the distal LV CS pace/sense electrode 50 alongside the LV chamber. The distal end of such LV CS leads is advanced through the superior vena cava, the right atrium, the ostium of the CS, the CS, and into a coronary vein descending from the CS, such as the cardiac vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiorly from the great vein 48.

In accordance with the present invention, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV.

Moreover, in a four-chamber embodiment, LV CS lead 52 could bear a proximal LA CS pace/sense electrode positioned along the lead body to lie in the larger diameter CS adjacent the LA. In that case, the lead body 56 would encase two electrically insulated lead conductors extending proximally from the more proximal LA CS pace/sense electrode (s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

FIG. 3A is a representational drawing of PVC 30, retrograde atrial event 31, and PVARP 30 to illustrate how retrograde event 31 falls within PVARP 33. The result of this operation of that retrograde atrial event 31 is treated as atrial refractory sensed event 34, due to the duration of the R-P interval. Any atrial events falling into blanking period 32 will not be sensed.

PVCs can occur in almost any human being. The issue with PVCs in pacemakers patients is the PVCs can result in pacemaker mediated tachycardias (PMTs), at a rate that is quite rapid, depending on the retrograde conduction interval, that is, the R-wave to P-wave interval. For the past several years, pacemaker manufacturers have extended the PVARP following a PVC so that most retrograde P-waves fall into the PVARP. When this happens, the retrograde P-wave is unable to initiate an AV interval. The extended PVARP intervention will, in most cases, prevent the initiation of a PMT. Unfortunately, however, some pacemaker patients have an R-P interval longer than the PVARP extension following a PVC. In such cases, the retrograde P-wave falls outside the programmed PVARP, initiates an AV interval, resulting in a paced R-wave. Thus, other types of interventions have been applied to "break" the PMT.

FIG. 3B illustrates a PMT. Retrograde P-waves 31, in this hypothetical case, fall outside the PVARP. As such, they start AV intervals that result in paced R-waves 35. However, if the patient were free of AV block, an intrinsic R-wave would have occurred at the end of intrinsic conduction time 38. However, in the presence of certain higher types of AV block, conduction does not occur. Thus the SAV interval times out, resulting in paced R-waves. Because the R-P interval is so short, the AV interval is extended 37 to ensure that the ventricles are not paced any faster than the upper tracking rate (UTR). Thus, paced ventricular events 35 that track the atrium can occur no faster than upper rate intervals 36.

If, however, the P-wave conducts, the result would be an intrinsic R-wave, rather than a paced R-wave. If an intrinsic R-wave occurs in a CHF patient, the result is a lack of ventricular synchronization. Atrial synchronized pacing is the reason why CHF implantable medical devices (IMD) are implanted. Intrinsic conduction in CHF patients results in non-synchronized ventricular depolarizations. To restore paced, synchronized ventricular depolarizations in such cases, a way must be found to shorten the total atrial refractory period (TARP) that is composed of the PVARP and sensed AV (SAV) interval.

Figure 4:
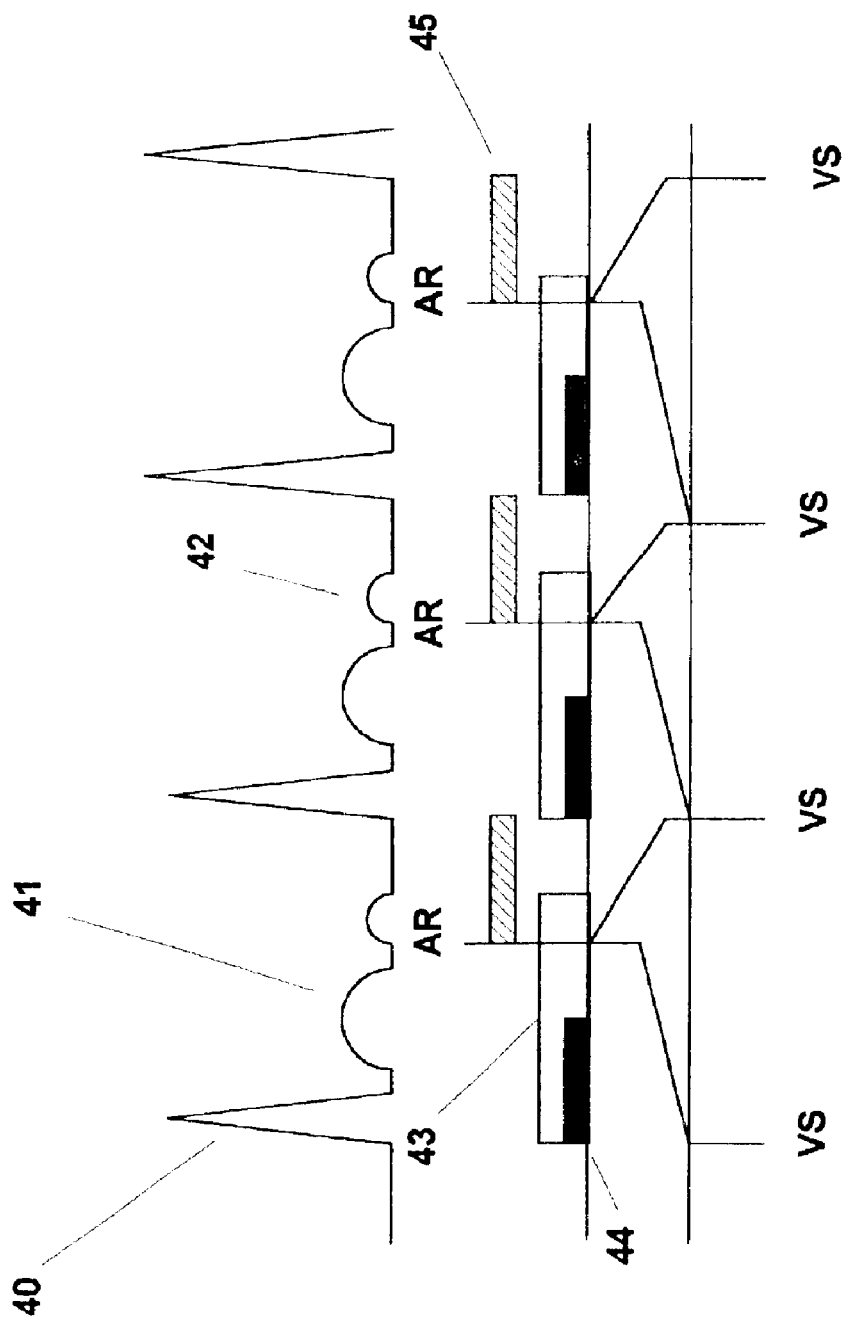
FIG. 4 is a representational drawing of ECG/EGM traces of cardiac activity showing how a conducted atrial refractory (AR) event results in a sensed intrinsic R-wave (VS).

FIG. 4 depicts an ECG that illustrates how a conducted atrial refractory event results in an intrinsic R-wave 40, thereby interrupting atrial-synchronized pacing. CHF patients generally do not have an AV conduction block. As a result, AR event 42 is conducted antegradely or retrogradely, as the case may be, through the AV conduction system resulting in an intrinsic R-wave 40 and T-wave 41. AR event falls within refractory period of PVARP 43 and is conducted 45 to the ventricle resulting in ventricular sensed event 40.

In all such cases, ventricular pacing must be restored. Since the R-P interval is a function of the heart, it is essential to shorten the PVARP 44 to ensure that the P-wave falls outside of the PVARP 44. By first shortening PVARP 44 only as much as is necessary to allow tracking of the next P-wave, the atrial event is changed from an AR to an Atrial sensed (AS) event. When this occurs, the AS will start an SAV, that is shorter than the patient's intrinsic conduction time, thereby allowing a paced ventricular event to occur and restore synchronized ventricular pacing.

Figure 5:
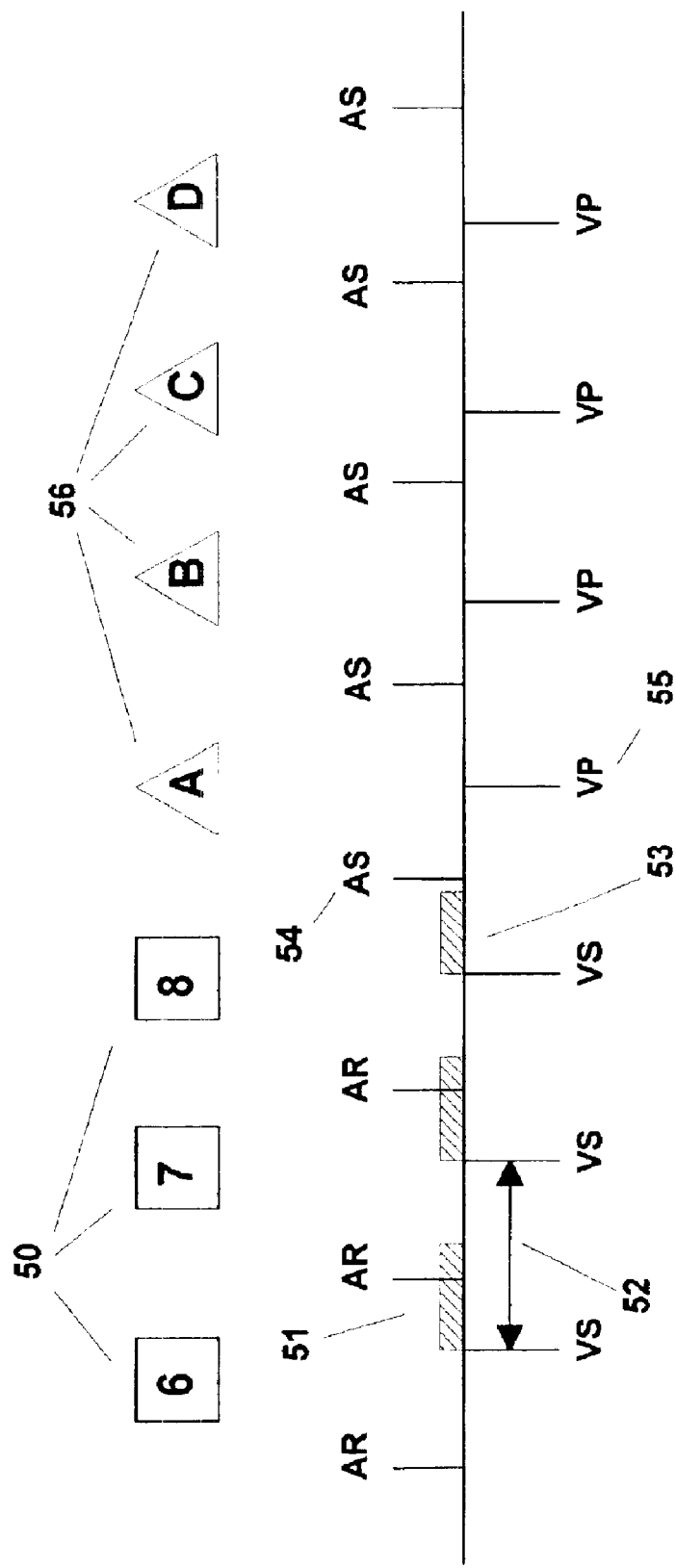
FIG. 5 is a temporal depiction of cardiac activity illustrating successful operation of the atrial tracking recovery (ATR) technique according to the present invention with restoration of atrial tracking, that is, AS-VP from following termination of a prior pattern of AR-VS cardiac activity.

FIG. 5 depicts a successful atrial tracking recovery (ATR) operation with restoration of atria tracking, that is, AS-VP. In this embodiment, AR-AR interval 52 within intervals 50 (6, 7, and 8) is 550 ms (109 bpm). The upper tracking rate interval (UTRI) is 500 ms (120 ppm). SAV is programmed to a short duration to ensure tracking during normal operation with a typical 310 ms PVARP 51. The algorithm uses 8 intervals 50 to establish a stable AR-VS pattern. After the eighth VS, PVARP 53 is shortened, for example, to 200 ms, among others. Due to the shortened PVARP, the atrial event is exposed, and is now sensed at 54. AS 54 starts SAV that is automatically extended to ensure that the UTRI is not violated, for example, it can be no shorter than 500 ms (for a programmed 120 ppm), resulting in VP 55. Following VP 55, the PVARP is extended a bit, such as 50 ms during interval A of sequence 56. AS at beginning of interval B of sequence 56 starts a shorter SAV. The VP within interval B starts a slightly longer PVARP compared to interval A while the SAV that starts interval C is again shortened. PVARP after VP within interval C is restored to its operating value of 310 ms. The AS at the beginning of interval D is now back to its programmed duration and is tracked without an upper rate hold-off. Normal operation follows thereafter.

Thus, by first altering the PVARP only to the extent required to unmask the P-wave and changing the SAV so that the UTR is not violated. UTR is able to successfully restore CRT. The PVARP is only shortened as needed and only for a short number of intervals. The device cannot pace above the clinician-programmed UTR. This last point is especially important for ICD-type devices. Because the UTR is not violated, the ability to detect VT/VF will not be compromised or delayed because of blanking due to high rate pacing.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, if may be replaced by any one of infinite equivalent alternatives, only some of which are disclosed in the specification. For example, the methods provided by the present invention may be implemented in a combination of hardware, software and/or firmware on a general purpose computer platform, a microprocessor-based platform or using a combination of RAM, ROM, EEPROM circuits and the like as is well known in the art. In the event the methods are thus performed instructions for performing said methods may be stored on a computer readable medium and executed as described and claimed herein.

We claimed:

1. A method of terminating a non-acing atrial refractory sense-ventricular sense (AR-VS) cardiac sequence and re-establishing a preferred pacing sequence, comprising:
    a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
    b) iteratively reducing the duration of the initial PVARP for a predetermined number of consecutive cardiac cycles until an intrinsic atrial event occurs following the PVARP and is sensed (AS) or a cardiac pattern other than an atrial refractory sense-ventricular sense (AR-VS) pattern occurs;
    c) delivering a ventricular pacing stimulus to the at least one ventricular chamber at the expiration of a sensed atrioventricular (SAV) delay interval; and
    d) extending the duration of the initial PVARP for at least a subsequent cardiac cycle and wherein the series of atrial refractory events (AR) that occur during the initial PVARP resulting in the sensing of intrinsic depolarization of the at least one ventricular chamber comprises at least five consecutive atrial refractory events (AR).

2. A method of terminating a non-pacing atrial refractory sense-ventricular sense (AR-VS) cardiac sequence and re-establishing a preferred pacing sequence, comprising:
    a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
    b) iteratively reducing the duration of the initial PVARP for a predetermined number of consecutive cardiac cycles until an intrinsic atrial event occurs following the PVARP and is sensed (AS) or a cardiac pattern other than an atrial refractory sense-ventricular sense (AR-VS) pattern occurs;
    c) delivering a ventricular pacing stimulus to the at least one ventricular chamber at the expiration of a sensed atrioventricular (SAV) delay interval; and
    d) extending the duration of the initial PVARP for at least a subsequent cardiac cycle and wherein the series of atrial refractory events (AR) that occur during an initial PVARP resulting in the sensing of intrinsic depolarization of the at least one ventricular chamber comprises at least eight consecutive atrial refractory events (AR).

3. A method of terminating a non-pacing atrial refractory sense-ventricular sense (AR-VS) cardiac sequence and re-establishing a preferred pacing sequence, comprising:
    a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
    b) iteratively reducing the duration of the initial PVARP for a predetermined number of consecutive cardiac cycles until an intrinsic atrial event occurs following the PVARP and is sensed (AS) or a cardiac pattern other than an atrial refractory sense-ventricular sense (AR-VS) pattern occurs;
    c) delivering a ventricular pacing stimulus to the at least one ventricular chamber at the expiration of a sensed atrioventricular (SAV) delay interval; and
    d) extending the duration of the initial PVARP for at least a subsequent cardiac cycle wherein at step e) returning to step a) in lieu of returning to step a), the following steps are performed;
    if an upper rate hold-off ventricular pace occurs due to an AV interval duration being longer than an operating SAV interval, and a maximum interval calculated in milliseconds based on a just prior cardiac cycle is less than an operating PVARP, declaring termination of the AR-VS pattern, wherein the maximum interval further comprises an A-A interval less a A-V interval less a 50 millisecond constant.

4. A method of terminating a non-pacing atrial refractory sense-ventricular sense (AR-VS) cardiac sequence and re-establishing a preferred pacing sequence, comprising:
    a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
    b) iteratively reducing the duration of the initial PVARP for a predetermined number of consecutive cardiac cycles until a intrinsic atrial event occurs following the PVARP and is sensed (AS) or a cardiac pattern other than an atrial refractory sense-ventricular sense (AR-VS) pattern occurs;
    c) delivering a ventricular pacing stimulus to the at least one ventricular chamber at the expiration of a sensed atrioventricular (SAV) delay interval; and
    d) extending the duration of the initial PVARP for at least a subsequent cardiac cycle and wherein at step e) returing to step a) in lieu of returning to step a), the following steps are performed:
    if an upper rate hold-off ventricular pace occurs due to an AV interval duration being longer than an operating SAV interval, and a maximum interval calculated in milliseconds based on a just prior cardiac cycle is greater than or equal to an operating PVARP, declaring termination of the AR-VS pattern, wherein the maximum interval further comprises the greater of an A-A interval less a A-V interval less a 50 millisecond constant or a post ventricular atrial blanking (PVAB) period;
    setting the operating PVARP to a maximum value; and returning to step b).

5. A method of termination a non-pacing atrial refractory sense-ventricular sense (AR-VS) cardiac sequence and re-establishing a preferred pacing sequence, comprising:
   a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
   b) iteratively reducing the duration of the initial PVARP for a predetermined number of consecutive cardiac cycles until an intrinsic atrial event occurs following the PVARP and is sensed (AS) or a cardiac pattern other than an atrial refractory sense-ventricular sense (AR-VS) pattern occurs;
   c) delivering a ventricular pacing stimulus to the at least one ventricular chamber at the expiration of a sensed atrioventricular (SAV) delay interval; and
   d) extending the duration of the initial PVARP for at least a subsequent cardiac cycle and wherein the initial PVARP is a maximum duration PVARP.

6. A method of terminating a non-acing atrial refractory sense-ventricular sense (AR-VS) cardiac sequence and re-establishing a preferred pacing sequence, comprising:
   a) monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
   b) iteratively reducing the duration of the initial PVARP for a predetermined number of consecutive cardiac cycles until an intrinsic atrial event occurs following the PVARP and is sensed (AS) or a cardiac pattern other than an atrial refractory sense-ventricular sense (AR-VS) pattern occurs;
   c) delivering a ventricular pacing stimulus to the at least one ventricular chamber at the expiration of a sensed atrioventricular (SAV) delay interval; and
   d) extending the duration of the initial PVARP for at least a subsequent cardiac cycle and wherein the initial PVARP is a previously manually programmed PVARP.

7. A computer readable medium for storing instructions for performing a method, comprising:
   a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
   b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;
   c) instructions for delivering a ventricular pacing stimulus to the at least one ventricular chamber at the expiration of a sensed atrioventricular (SAV) delay interval; and
   d) instructions for extending the duration of the initial PVARP for at least a subsequent cardiac cycle and wherein the series of atrial refractory events (AR) that occur during the initial PVARP resulting in the sensing of intrinsic depolarization of the at least one ventricular chamber comprises at least five consecutive atrial refractory events (AR).

8. A computer readable medium for storing instructions for performing a method, comprising:
   a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
   b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;
   c) instructions for delivering a ventricular pacing stimulus to the at least one ventricular chamber at the expiration of a sensed atrioventricular (SAV) delay interval; and
   d) instructions for extending the duration of the initial PVARP for at least a subsequent cardiac cycle and wherein the series of atrial refractory events (AR) that occur during an initial PVARP resulting in the sensing of intrinsic depolarization of the at least one ventricular chamber comprises at least eight consecutive atrial refractory events (AR).

9. A computer readable medium for storing instructions for performing a method, comprising:
   a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;
   b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;
   c) instructions for delivering a ventricular pacing stimulus to the at least one ventricular chamber at the expiration of a sensed atrioventricular (SAV) delay interval; and
   d) instructions for extending the duration of the initial PVARP for at least a subsequent cardiac cycle and wherein at step e) instructions for returning to step a) in lieu of instructions for returning to step a), the following steps are performed:
   if an upper rate hold-off ventricular pace occurs due to an AV interval duration being longer than an operating SAV interval, and a maximum interval calculated in milliseconds based on a just prior cardiac cycle is less than an operating PVARP, instructions for declaring termination of the AR-VS pattern, wherein the maximum interval further comprises an A-A interval less an A-V interval less a 50 millisecond constant.

10. A computer readable medium for storing instructions for performing a method, comprising:
   a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;

b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;

c) instructions for delivering a ventricular pacing stimulus to the at least one ventricular chamber at the expiration of a sensed atrioventricular (SAV) delay interval; and d) instructions for extending the duration of the initial PVARP for at least a subsequent cardiac cycle and wherein at step e) instructions for returning to step a) in lieu of instructions for returning to step a), the following steps are performed:

if an upper rate hold-off ventricular pace occurs due to an AV interval duration being longer than an operating SAV interval, and a maximum interval calculated in milliseconds based on a just prior cardiac cycle is greater than or equal to an operating PVARP, instructions for declaring termination of the AR-VS pattern, wherein the maximum interval further comprises an A-A interval less an A-V interval less a 50 millisecond constant;

instructions for setting the operating PVARP to a maximum value; and returning to step b).

11. A computer readable medium for storing instructions for performing a method, comprising:

a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of that at least one ventricular chamber;

b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;

c) instructions for delivering a ventricular pacing stimulus to the at least one ventricular chamber at the expiration of a sensed atrioventricular (SAV) delay interval; and d) instructions for extending the duration of the initial PVARP for at least a subsequent cardiac cycle and wherein the initial PVARP is a maximum duration PVARP.

12. A computer readable medium for storing instructions for performing a method, comprising:

a) instructions for monitoring an atrial chamber and at least one ventricular chamber for delivery of a pacing therapy and for sensing of intrinsic depolarization activity and, in the event that a series of atrial refractory events (AR) occur during an initial post-ventricular atrial refractory period (PVARP) resulting in the sensing of intrinsic depolarizations of the at least one ventricular chamber;

b) instructions for iteratively reducing the duration of the initial PVARP for a predetermined number of consecutive cardiac cycles until an intrinsic atrial event occurs following the PVARP and is sensed (AS) or a cardiac pattern other than an atrial refractory-sense-ventricular sense (AR-VS) pattern occurs;

c) instructions for delivering a ventricular pacing stimulus to the at least one ventricular chamber at the expiration of a sensed atrioventricular (SAV) delay interval; and d) instructions for extending the duration of the initial PVARP for at least a subsequent cardiac cycle and wherein the initial PVARP is a previously manually programmed PVARP.

* * * * *

UNITED STATES PATENT AND TRADEMARK OFFICE
CERTIFICATE OF CORRECTION

PATENT NO. : 6,889,083 B2
APPLICATION NO. : 10/419593
DATED : May 3, 2005
INVENTOR(S) : Kleckner et al.

It is certified that error appears in the above-identified patent and that said Letters Patent is hereby corrected as shown below:

Col. 11, line 16, please delete "non-acing atrial" and insert --non-pacing atrial--.

Col. 12, line 44, please delete "until a intrinsic" and insert --until an intrinsic--.

Col. 13, line 1, please delete "of termination" and insert --of terminating--.

Col. 13, line 24, please delete "a non-acing" and insert --a non-pacing--.

Col. 16, line 1, please delete "of that at" and insert --of the at--.

Signed and Sealed this

Nineteenth Day of December, 2006

JON W. DUDAS
*Director of the United States Patent and Trademark Office*